US00PP09991P

United States Patent [19]

Kientzler

[11] Patent Number: Plant 9,991

[45] Date of Patent: Aug. 5, 1997

[54] IMPATIENS PLANT NAMED 'DOMINICA'

[75] Inventor: Ludwig Kientzler, Gensingen, Germany

[73] Assignee: Paul Ecke Ranch, Inc., Encinitas, Calif.

[21] Appl. No.: 620,956

[22] Filed: Mar. 25, 1996

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 6,925 7/1989 Kientzler ..... Plt./87.6

P.P. 8,400 9/1993 Kientzler ..... Plt./87.6

*Primary Examiner*—Howard J. Locker

*Attorney, Agent, or Firm*—Foley & Lardner

[57] ABSTRACT

A new cultivar of Impatiens plant named Dominica, characterized by its compact growth habit with excellent branching, large purplish-red flowers having a diameter of up to 6.5 cm, very floriferous habit; green, glossy foliage, and its adaptability to 4" pot, 6" pot, and 8" hanging basket culture.

1 Drawing Sheet

1

The present invention relates to a new and distinct cultivar of plant known as Impatiens and commercially kown as New Guinea Impatiens. The new cultivar is known by the cultivar name Dominica, and was developed by the inventor Ludwig Kientizler in Gensingen, Federal Republic of Germany by crossing the cultivar designated B V 443 (seed parent) with the cultivar G Z 991 (pollen parent).

Asexual reproduction by terminal (stem tip) cuttings taken by or under the supervision of the inventor at Gensingen, Federal republic of Germany, has shown that the unique features of this new impatiens are stabilized and are reproduced true to type in successive propagations.

The following characteristics distinguish the new impatiens from both its parent varieties and other cultivars of this general type known and used in the floriculture industry:

1. Compact growth habit with excellent branching characteristics. Plants in 16.5 cm pots were 19 cm tall and 30 cm wide, eight (8) weeks after first flowering.

2. Large, purplish-red flowers. Open flowers measure up to 6.5 cm in diameter.

3. Very floriferous. Plants in 16.5 cm pots were in flower seven (7) weeks after planting.

4. Green, glossy foliage.

5. Well suited to 4" pot, 6" pot and 8" hanging basket culture.

Dominica is similar in many respects to Papete, disclosed in U.S. Plant Pat. No. 8,457. The flower color of Dominica is similar to Papete but a little darker and with less red tones. The leaf color of Dominica is a little lighter than Papete. In addition, Dominica has a more vigorous growth habit, larger flowers and blooms later than Papete. The leaf petiole color of Dominica (R.H.S. 59A) is darker than Papete (R.H.S. 53A). The under leaf surfaces of Papete have setae on the veins; Dominica does not. These differences are based on comparisons made in May 1995 based on plants of the same age and in full flower.

The accompanying colored photographic drawing is a top perspective view of the new cultivar, showing color as true as it is reasonably possible to obtain in a colored reproduction of this type.

The following is a detailed description of the new impatiens cultivar based on plants grown under commercial practice in Encinitas, Calif. Plants were started as rooted cuttings and were transplanted in mid-February into 16.5 cm

2

(6.5 inch) pots, one pot per plant. By mid-April, plants were growing vigorously and were in flower. The values, measurements and observations noted below were taken from plants in full bloom in mid-May.

Color references are made to The Royal Horticultural Society Colour Chart (R.H.S.), except where general terms of ordinary dictionary significance are used.

Parentage: Cross between B V 443 (seed) and G Z 991 (pollen).

Asexual reproduction:

*Cutting type.*—Tip, with stems 2–3 cm long and developing to 4–5 cm after 21 days in propagation.

*Time to initiate roots.*—8–10 days at 23° C.; nicely developed root mass in 18–21 days.

*Rooting habit.*—Numerous, fibrous, adventitious roots from the stem.

Plant description:

*Form.*—Symmetrical, bush shaped, flowering herb, with self-branching characteristics giving the plant a full appearance. Pinching is not recommended since it does not enhance branching and only delays flowering by removing flower buds.

*Habit of growth.*—Vigorous, self-branching habit, producing whorls of leaves and flowers. Growth is indeterminate and flowering is continuous.

*Foliage description.*—Leaves are simple. Lower leaves on stems in whorls of 2–3. Higher on stem, leaves in whorls of mostly 5. Leaf shape: Broadly elliptic to ovate. Leaf blade tips are acuminate; bases of immature leaves are acute, mature leaves attenuate. Leaf blade size: Mature leaves 8–10 cm long and 3–4 cm wide. Petiole length: About 1.5 cm. Leaf margin: Ciliated and finely serrated. Leaf texture: slightly rugose. Upper surface: Glabrous. Under surface: Glabrous. Leaf color: Green with a red midvein. Upper surface: Near 137A. Midvein near 59A. Under surface: Green 191A-B. Red veins. Venation: Pinnate.

Flowering description:

*Flowering habits.*—Very floriferous. Flowering is continuous. Flowers develop progressively around the whorl of leaves, taking 5–7 days from buds that show color, to bloom. Flowers are single and large, lasting for 2–3 weeks.

*Natural flowering season.*—Flowering is indeterminate and occurs throughout the year. Quantity of flowers increases with increasing light intensity and duration. However, floriferousness may wane during hot summer days in temperate climates.

*Flower buds.*—Ellipsoidal and covered with three (3) sepals plus rudimentary sepals fused into the under surface of the superior petal. A spur originates from the base of the inferior sepal. Spur is red and about 5 cm long.

*Flowers borne.*—Singly, on dark red pedicels 4–5 cm long.

*Quantity of flowers.*—One flower per leaf. Flowers occur progressively around the whorl of leaves so that tight buds to mature flowers are visible at the same time.

*Petals.*—Petals open less than perpendicular to the pedicel so that the plane of the flower surface is slightly cupped. Number of petals: Five (5) petals, all overlapping. Shape: All petals are heart-shaped. Superior petal has a broad base. Other petals have a pointed base. Color: Purplish red petals. Upper surface: Darker than 74A. Under surface: 66A-67A. Flower size: Up to 6.5 cm in diameter.

*Reproductive organs.*—Stamens: Five (5), broad and fused to form a tube around the ovary; red in color. Anther: Hooded and cream colored. Pollen: Cream colored. Stigma: Five-pointed star, colorless. Styles: Very short. Ovary: Five-celled, 4–5 mm long until fertilized. Grows to 1 cm or longer after fertilization; purplish.

Resistance to disease: Good resistance to common stem and root diseases, Rhizoctonia and Pythium. Botrytis may be a problem in humid or mist propagation environments, but no greater than with other New Guinea Impatiens cultivars.

It is claimed:

1. A new distinct cultivar of Impatiens plant named Dominica, as illustrated and described.

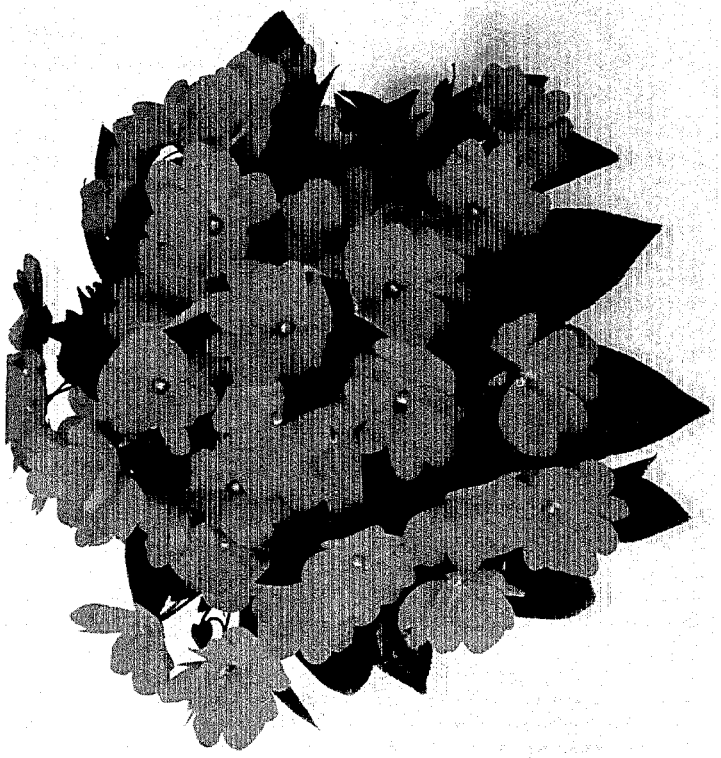

* * * * *